US008790917B2

(12) United States Patent
Kriz et al.

(10) Patent No.: US 8,790,917 B2
(45) Date of Patent: Jul. 29, 2014

(54) DEVICE FOR BIOCHEMICAL PROCESSING AND ANALYSIS OF A SAMPLE

(75) Inventors: Dario Kriz, Höör (SE); Kirstin Kriz, Höör (SE)

(73) Assignee: Lifeassays AB, Lund (SE)

( * ) Notice: Subject to any disclaimer, the term of this patent is extended or adjusted under 35 U.S.C. 154(b) by 868 days.

(21) Appl. No.: 12/734,589

(22) PCT Filed: Oct. 24, 2008

(86) PCT No.: PCT/SE2008/051206

§ 371 (c)(1),
(2), (4) Date: May 11, 2010

(87) PCT Pub. No.: WO2009/064241

PCT Pub. Date: May 22, 2009

(65) Prior Publication Data

US 2010/0255460 A1 Oct. 7, 2010

(30) Foreign Application Priority Data

Nov. 12, 2007 (SE) ........................................ 0702489

(51) Int. Cl.
*C12M 3/00* (2006.01)

(52) U.S. Cl.
USPC ........................................................ 435/287.6

(58) Field of Classification Search
None
See application file for complete search history.

(56) References Cited

U.S. PATENT DOCUMENTS 3,811,326 A 5/1974 Sokol
4,935,020 A 6/1990 Brodén
5,658,531 A * 8/1997 Cope et al. .................... 422/410
5,833,630 A 11/1998 Kloth
5,888,826 A * 3/1999 Ostgaard et al. ................ 436/69
6,110,660 A 8/2000 Kriz et al.
6,319,209 B1 11/2001 Kriz
7,118,626 B2 * 10/2006 Ng et al. ......................... 117/68
2001/0001060 A1 * 5/2001 Kellogg et al. ................ 435/7.1
2002/0016320 A1 * 2/2002 Fang et al. ............... 514/211.15
2004/0161368 A1 * 8/2004 Holtlund et al. ............. 422/68.1
2005/0130291 A1 * 6/2005 Erhardt et al. ............. 435/287.1
2005/0142031 A1 * 6/2005 Wickstead et al. .............. 422/58
2007/0270710 A1 * 11/2007 Frass et al. .................... 600/567
2009/0216213 A1 * 8/2009 Muir et al. .................... 604/414

FOREIGN PATENT DOCUMENTS

SE 451 942 11/1987
SE 9502902-1 6/2003
WO WO 79/01131 * 5/1979 ............... A61B 5/14
WO WO 79/01131 A1 12/1979
WO WO 7901131 * 12/1979 ............... A61B 5/14
WO WO 01/13795 A1 3/2001

OTHER PUBLICATIONS

Kriz, K. et al., "Detection of C-Reactive Protein Utilizing Magnetic Permeability Detection Based Immunoassays", Analytical Chemistry , Sep. 2005, vol. 77, pp. 5920-5924.
Larsson, K, et al., "Magnetic Transducers in Biosensors and Bioassays", Analusis, 1999, vol. 27, No. 7, pp. 617-621.
International Search Report, for PCT/SE2008/051206.

* cited by examiner

*Primary Examiner* — Ann Lam
(74) *Attorney, Agent, or Firm* — Harness, Dickey & Pierce, P.L.C.

(57) ABSTRACT

A device for biochemical processing and analysis of a measured sample volume of a sample is described. The device is characterized in that it consists of a sealed vessel (1) and that it comprises at least one thin pierceable membrane (2) through which a capillary tube (3) containing said measured sample volume of a sample can pass into said sealed vessel (1). Said sealed vessel (1) further contains at least one biochemically reactive substance (4) and a liquid (6). A method, wherein the device according to the invention is used for analysis, is also described.

18 Claims, 2 Drawing Sheets

DEVICE FOR BIOCHEMICAL PROCESSING AND ANALYSIS OF A SAMPLE

FIELD OF THE INVENTION

The present invention relates to a disposable device for biochemical processing and analysis of a measured sample volume of a liquid sample. The invention is especially intended to be used for qualitative and quantitative biochemical analysis of body fluids (inter alia blood and urine) in near patient measurements but can also be used for analysis of other liquid samples in industrial process control, quality control as well as research and laboratory work.

BACKGROUND ART

A large number of near patient analyses are performed every day in hospitals, in primary health care and at home. In a frequent method, a measured sample volume of the patient's body fluid (for instance blood, plasma, urine, sweat, tears, lymph, amniotic fluid, cerebrospinal fluid and faeces) is collected in a capillary tube and transferred to a container, after which it is exposed to various specific reagents with which the body fluid reacts. The final quantitative or qualitative chemical analysis is performed by means of an optical detector in a transparent cuvette or on a measuring surface. The devices (for instance QuikRead manufactured by Axis Shield A/S, Norway) which are based on a manual method imply that the sample volume and reagent solutions may be spilt on people or work surfaces, resulting in health and environmental hazards. There is also a risk of incorrect analytical results due to laboratory mishandling. The devices (for instance Afinion manufactured by Axis Shield A/S, Norway) which are based on automated methods reduce the above-mentioned health and environmental hazards and also the risk of incorrect analytical results, but this is done by a costly and complex technical solution.

The specific reagents that are used are of the type biochemically (that is biologically and chemically) reactive substances, which may consist of monoclonal antibody, polyclonal antibody, enzyme, inorganic oxidising agents, inorganic reducing agents, metal ions, metal ion complexes, proteins, hormones, complementary factors, bacteria, cells, virus, fungi, yeast, spores, phages, cell organelles, peptides, DNA, RNA, coagulation inhibiting substances, cell lysing agents, antibiotics, tenside and active detergents.

After the body fluid having reacted with one or more specific reagents, this biological or chemical event is transformed into a physical change (optical, electric, radioactive or magnetic), which can be perceived by a detector. Optical detectors are popular especially in established immunoassay technologies that are used for near patient analyses. Optical detectors measure, inter alia, changes of the absorption of light, light scattering, fluorescence, polarisation, and require transparent cuvettes with transparent liquid sample contents. This results in the drawback that the liquid sample frequently has to be biochemically processed in several steps before it reaches the transparent cuvette or measuring surface. Electric detectors must be in direct contact with the liquid sample and therefore are sensitive to disturbing substances such as ascorbic acid in the body fluid. Radioactive detectors are rare in near patient analyses since they are a danger to people and environment. Magnetic detectors measure, inter alia, magnetic permeability and have the advantage that they allow quick and easy detection of the contents in non-transparent cuvettes which are allowed to contain non-transparent fluid, suspension, and capillary tubes. Such a magnetic detector is disclosed in SE9502902-1, U.S. Pat. No. 6,110,660 and Larsson K. et al. Analusis 27, p 78 1999.

The present invention solves the above described problems in a new and effective way by offering the user a manually operable disposable device to provide leakage-free biochemical processing and analysis of a measured sample volume of a liquid sample with an eliminated risk of contamination of people and environment and a minimised risk of incorrect measured values without using instruments with automatic preparation of samples.

The above-mentioned commercially available devices and documents SE9502902-1 (Dario Kriz, 1995) U.S. Pat. No. 6,110,660 (Dario Kriz, 1995) and Larsson K. et al. (Analusis 27, p 78, 1999) describe prior art devices and methods that are used for chemical processing and analysis of a measured sample volume of a liquid sample. However, said devices and methods do not contain a thin pierceable membrane through which an arm-fixed capillary tube passes and fits tightly around the arm after the insertion of the capillary tube. The present invention enables a manually operable disposable device to provide leakage-free biochemical processing and analysis of a measured sample volume of a liquid sample with an eliminated risk of contamination of people and environment and a minimised risk of incorrect measured values due to reagent losses related to leakage of liquid without using instruments with automatic preparation of samples and without necessitating a negative pressure or an injection mechanism in the inventive device.

Other prior art techniques comprise a liquid sample collecting device according to WO 79/01131 (Robert Turner and Reginald Holman, 1978). This device comprises a pierceable flexible membrane which is penetrated by a capillary tube. The membrane fits tightly around the capillary tube, of which each end is on an associated side of the membrane. To allow the sample volume in the capillary tube to be drawn into the device there is a negative pressure in the device. The present invention does not require a negative pressure since both ends of the capillary tube pass the membrane and the sample volume is shaken out of the capillary tube. Furthermore the device according to WO 79/01131 doe not contain any substances for biochemical processing and analysis.

Other prior art techniques comprise a sample collecting device according to U.S. Pat. No. 5,833,630 (Bernd Kloth, 1997). This device comprises a capillary tube and substances for biochemical processing and analysis. The device does not comprise a pierceable membrane which is penetrated by the capillary tube. The capillary tube is positioned in a duct in a stopper which is placed on the device. The capillary tube is pressed into (but not through) the stopper by means of a cap, the generated positive pressure forcing the sample volume out of the capillary tube and down into the device. Since the device does not have a pierceable membrane and requires manual exchange of the stopper (from a stopper without capillary tube to one with capillary tube), there is a risk of some spilling of the reagent solution of the device, which results in incorrect measured results. Moreover the emptying of the capillary tube will not be as quick and effective as in the present invention since the forced liquid movement through the capillary tube in the present invention cleans the capillary tube without leaving any residues of adsorbed sample solution.

Other prior art techniques comprise a device for handling organic body fluids according to SE451942 (Bengt-Inge Brodén, 1986). This device comprises a capillary tube but no substances for biochemical processing and analysis. The device does not comprise a pierceable membrane which is penetrated by the capillary tube. The capillary tube is positioned in a duct in a stopper which is placed on the device. Air is forced through the capillary tube by means of a sprayer, the generated positive pressure forcing the sample volume out of the capillary tube and down into the device. The device does not contain any substances for chemical processing and analysis and is designed to reduce the risk of contamination caused by spilling of body fluid samples. Furthermore the emptying of the capillary tube will not be as quick and effective as with the present invention since the forced liquid movement through the capillary tube in the present invention cleans the capillary tube without leaving any residues of adsorbed sample solution.

Other prior art techniques comprise a combination reagent and test device for analysing liquids according to U.S. Pat. No. 5,888,826 (Roy Ostgaard et el., 1997). This device comprises a pierceable membrane and substances for biochemical processing and analysis. The device does not comprise a capillary tube and is not designed for manual handling (mixing of sample solution and reagent) but requires advanced automatic instruments for function.

Other prior art techniques comprise a disposable device for analysing liquids according to U.S. Pat. No. 6,319,209 (Dario Kriz, 1999). This device comprises a capillary tube and substances for biochemical processing and analysis. Since the device does not have a pierceable membrane and requires manual turning of a stopper (from one without to one with capillary tube) there is a risk of some spilling of the reagent solution of the device, which results in incorrect measured results. Moreover the emptying of the capillary tube will not be as quick and effective as in the present invention since the forced liquid movement through the capillary tube in the present invention cleans the capillary tube without leaving any residues of adsorbed sample solution.

SUMMARY OF THE INVENTION

Thus the present invention relates to a device, characterised in that it comprises a sealed vessel (1), which contains at least one thin pierceable membrane (2), through which a capillary tube (3) fixed to an arm (9) can pass into the vessel. When the arm (9) has inserted the capillary tube (3) into the vessel (1), the opening in the membrane (2) is sealed by the rear part of the arm (9). The sealed vessel (1) contains, in addition to a liquid (6), at least one biochemically active substance (4) and/or at least one marker substance (5) and/or a sediment of carrier particles (7) depending on which quantitative or qualitative chemical analysis is to be performed.

The invention also relates to a method in which a device according to the invention is used to empty, by shaking (both manually and automatically), the contents of the capillary tube (3) into the vessel (1) to begin the biochemical processing and analysis of the measured sample volume of a liquid sample. The invention further concerns a method in which a device according to the invention after shaking is placed in an instrument comprising a detector for reading of physical changes for the purpose of performing qualitative or quantitative analyses of various biological or chemical substances.

DETAILED DESCRIPTION OF THE INVENTION

Figure 1:
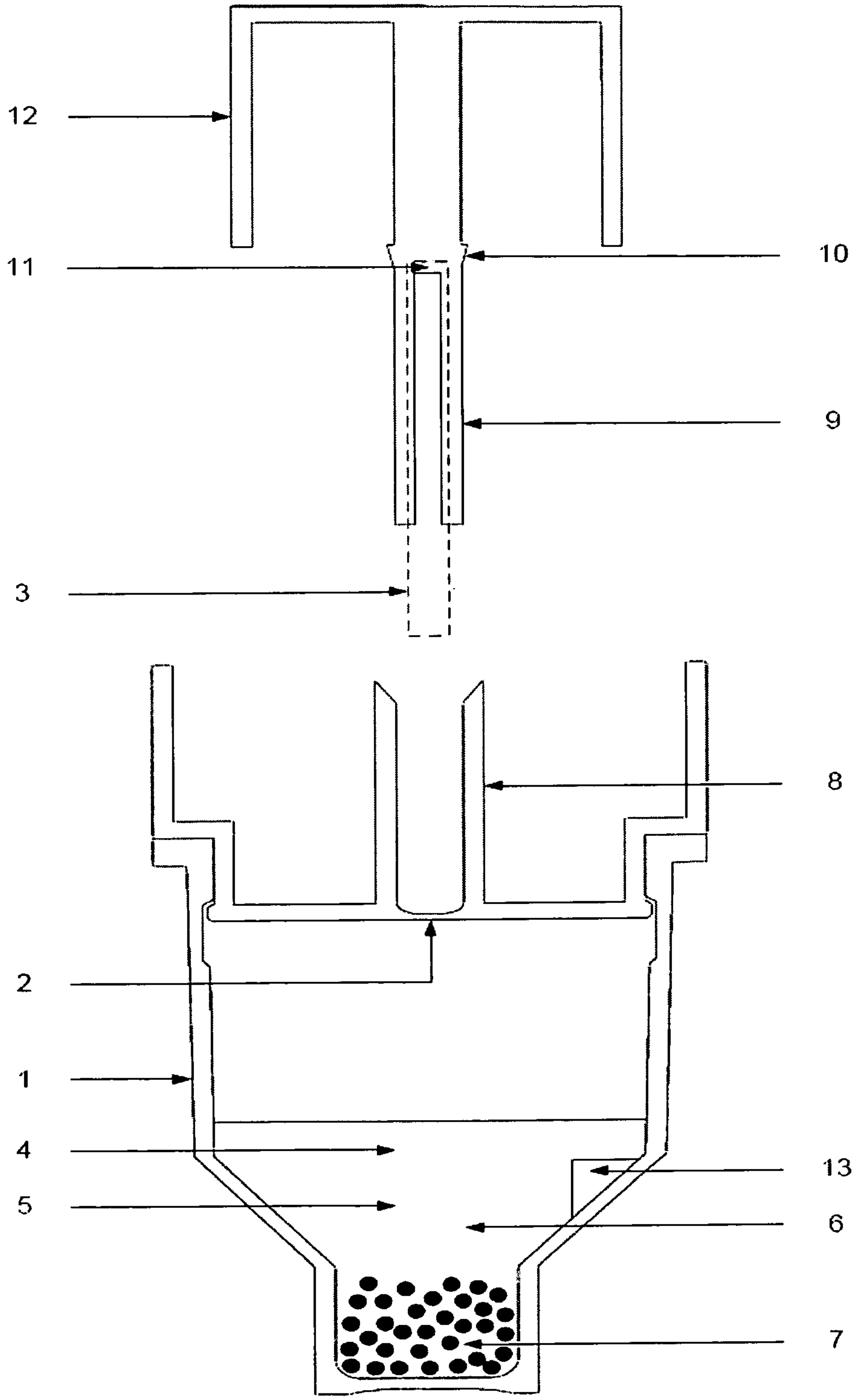
FIG. 1 illustrates the device according to the present invention with an intact pierceable membrane (2) and the capillary tube (3) attached to the arm (9).

According to one aspect of the invention, the device is characterised in that the sealed vessel (1) has a volume in the range 0.1-250 ml and that it contains a liquid (6), and that the thickness of the thin pierced membrane (2) is in the range 0.01-5 mm, and that the thin pierced membrane (2) is attached in a circular opening adapted to fit tightly against the arm (9) and has a diameter in the range 0.5-5 mm, and that the capillary tube (3) has a length in the range 1-30 mm, and that the capillary tube (3) has an outer diameter in the range 0.2-3 mm, and that a filled capillary tube (3) may contain a measured sample volume in the range 0.1-200 μl, and that the collar (8), which facilitates the insertion of the capillary tube (3), has a length in the range 1-20 mm.

According to another aspect, the device is characterised in that the sealed vessel (1) contains one or more biochemically reactive substances (4), which may consist of monoclonal antibody, polyclonal antibody, enzyme, inorganic oxidising agents, inorganic reducing agents, metal ion, metal ion complex, protein, hormone, complementary factor, bacterium, cell, virus, fungus, yeast, spore, phage, cell organelle, peptide, DNA, RNA, coagulation inhibiting substance, cell lysing agents, antibiotics, tenside, active detergent, EDTA, adenosine 5' diphosphate, ristocetin, arachidonic acid, thrombin, epinephrine, platelet activator factor or thrombin receptor agonist peptide (TRAP). The biochemically reactive substances (4) that are used depend on what analysis is to be performed and have generally known and well-documented functions, which comprise, for example, binding to the biological or chemical substance that is to be determined, catalytic conversion of the biological or chemical substance that is to be determined, stabilisation of the contents in the sealed vessel (1) so as to allow long-term storage, stabilisation of the biological or chemical substance that is to be determined once it is inserted in the sealed vessel (1) so that correct analytical results can be obtained, deactivation of disturbing biological or chemical substances that may disturb the measurement, and cell lysis or release of the biological or chemical substance that is to be determined so as to obtain correct analytical results.

According to another aspect, the device is characterised in that the sealed vessel (1) contains one or more marker substances (5), which may consist of magnetically influenceable reagents, such as superparamagnetic nanoparticles, antibody-derivatised superparamagnetic nanoparticles, protein-derivatised superparamagnetic nanoparticles, polymer-derivatised superparamagnetic nanoparticles, peptide-derivatised superparamagnetic nanoparticles, DNA- or RNA-derivatised superparamagnetic nanoparticles, carbohydrate-derivatised superparamagnetic nanoparticles, or alternatively that the marker substance (5) consists of an optical, electric or radioactive reagent based on antibodies, enzymes, inorganic oxidising agents, inorganic reducing agents, metal ions and metal ion complexes, proteins, peptides, polymers, carbohydrates, complementary factors, blood coagulation factors, hormones, bacteria, cells, viruses, fungi, yeast, spores, phages, cell organelles, DNA, RNA, coagulation inhibiting substances, antibiotics, tenside and active detergent. The marker substances (5) that are used depend on what analysis is to be performed and have generally known and well-documented functions which comprise interaction with the biological or chemical substance that is to be determined and generation of a quantifiable physical change (optical, electric, radioactive or magnetic), which can be perceived by a detector.

According to yet another aspect, the device is characterised in that the contents in the sealed vessel (1) have a relative magnetic permeability ($\mu_r$, which is increased relative to water and which is in the range $1.00001<\mu_r<10$.

According to a further aspect, the device is characterised in that the carrier particles (7) have antibodies or alternatively lectines, or alternatively proteins, or alternatively peptides, or alternatively DNA or RNA, or alternatively nothing bound to their surface and have a diameter between 0.5 micrometer and 5 mm and can consist of hydrophilic silica, hydrophobic silica, glass, silicon dioxide, carbohydrates, ion exchangers, polymers, ceramic materials, proteins, bacteria. The carrier particles (7) that are used depend on what analysis is to be performed and have generally known and well-documented functions, which comprise binding and enriching of the biological or chemical substance with which the marker substance (5) is associated and which thus accumulates a quantifiable physical change (optical, electric, radioactive or magnetic) in the bottom sediment which can be perceived by a detector.

According to another aspect, the device is characterised in that said liquid (6) consists of an aqueous solution containing at least one acidity regulating agent, such as 0.1 M sodium phosphate pH 7, and at least one ionic strength adjusting agent, such as 0.1 M sodium chloride. The liquid (6) that is used depends on what analysis is to be performed and has generally known and well-documented functions, which comprise, for example, dissolution of proteins, salts and sample liquid for an analysis to be performed. Moreover, the liquid (6) satisfies the requirements in respect of salt content and pH (acidity) which are placed on the matrix by the biochemically reactive substances (4), the marker substances (5) and the carrier particles (7) due to their function and which influence stability, cell-cell interactions, cell-ligand interactions, antibody-antigen interactions, binding, catalytic capacity and enzymatic activity.

According to a further aspect, the device is characterised in that it is fitted with a capillary holder which comprises an arm (9) of plastic, in which a capillary tube (3) of glass is mounted, or alternatively that the arm (9) is a unit which also has the form of a capillary tube (3). The capillary tubes (3) that are used depend on the sample volume that is to be measured and have generally known and well-documented functions, which comprise chemical material compatibility with the biological or chemical substance and the liquid sample that is to be analysed.

According to yet another aspect, the device is characterised in that it is fitted with a capillary holder which comprises an arm (9), said arm (9) having a conically shaped thickening of the outer diameter or that it has a collar (10), by which the opening in said thin pierceable membrane is sealed after the insertion of the capillary tube (3).

According to a further aspect, the device is characterised in that it is fitted with a capillary holder which comprises an arm (9), said arm (9) having an air vent (11) in the form of a hole (with the diameter 0.2-5 mm) or alternatively in the form of a gap (having the width 0.2-5 mm and the length 1-20 mm) which extends parallel to the capillary tube and through which pressure equalisation occurs so as to allow filling of said capillary tube (3).

According to another aspect, the device is characterised in that it is fitted with a capillary holder which also comprises a cap (12), which facilitates the handling of the capillary tube (3) and the height of which in the range 1-20 mm is adjusted to the length of said arm (9) and the location of the capillary tube (3) on said arm (9) so as to allow the insertion of the capillary tube (3) into said sealed vessel (1) in a predetermined and reproducible manner, implying that the conically shaped thickening of the outer diameter or alternatively the collar (10) forms, with the opening in said thin pierceable membrane, a hermetic and/or leakage-free seal after the insertion of the capillary tube (3).

According a further aspect, the device according to the invention is characterised in that the vessel (1) comprises at least one internal wing (13), which facilitates the emptying, by shaking (both manually and automatically), the contents of the capillary tube (3) into the vessel (1) to begin the biochemical processing and analysis of the measured sample volume of a sample. The emptying of the capillary content is facilitated by increased fluid turbulences caused by the at least one internal wing (13). This results in that the mixing of the liquid and sample in the device is facilitated.

According to one aspect, the internal wing (13) has a length and width in the range of 0.2-5 mm and a thickness in the range of 0.2-5 mm.

According to a further aspect, the device according to the invention is characterised in that the material of which said sealed vessel (1), said thin pierceable membrane (2), said capillary holder and said capillary tube (3) are made is one or a combination of the following materials, such as polymers, for instance Delrin, Perspex, POM, polyvinylchloride, polyvinyl fluoride, Teflon, polyamide, polyacetal, nylon, polyethylene, polycarbonate, polystyrene, and polypropylene, or alternatively a material such as glass, rubber, wood, paper and metal.

According to a further aspect, the device according to the inventions is characterised in that the material of which said sealed vessel (1) and/or said thin pierceable membrane (2) are made is a non-transparent material, for instance black polymer, for the purpose of protecting light-sensitive biochemically reactive substances (4) from being detrimentally affected by light in long time storage of the device. The use of a non-transparent material is compatible with magnetic detectors (and not with optical detectors) since their measuring process is not disturbed.

According to a further aspect, the device according to the invention is characterised in that said samples consist of body fluids such as blood, plasma, urine, sweat, tears, lymph, amniotic fluid, cerebrospinal fluid and faeces.

According to another aspect, the device according to the invention is characterised in that measured volumes of said sample, when consisting of faeces, can be manually pressed into the cavity of the capillary tube (3) without the use of capillary forces.

FIG. 1 is a view (on a scale of 1:3, that is 30 mm in the figure corresponds to 10 mm in real life) of the device according to the present invention. The device according to FIG. 1 comprises an intact pierceable membrane (2) of polypropylene and the capillary tube (3) of glass is attached to the arm (9) of polycarbonate. The sealed vessel (1) of polypropylene contains a liquid (6) consisting of 0.1 M sodium phosphate buffer pH 7.0 with 0.1 M sodium chloride, and a biochemically active substance (4) (EDTA) which prevents blood coagulation, and a marker substance (5) consisting of antiCRP monoclonal antibodies coupled to superparamagnetic nanoparticles, and a bottom sediment of carrier particles (7) consisting of antiCRP polyclonal antibodies coupled to silica particles with a diameter 15-40 μm, and a collar (8) of polypropylene. Further the device according to FIG. 1 comprises a capillary holder with the arm (9), which fixes the capillary tube (3) and the cap (12) of polycarbonate. The arm (9) also comprises a collar (10) of polycarbonate and an air vent (11).

Figure 2:
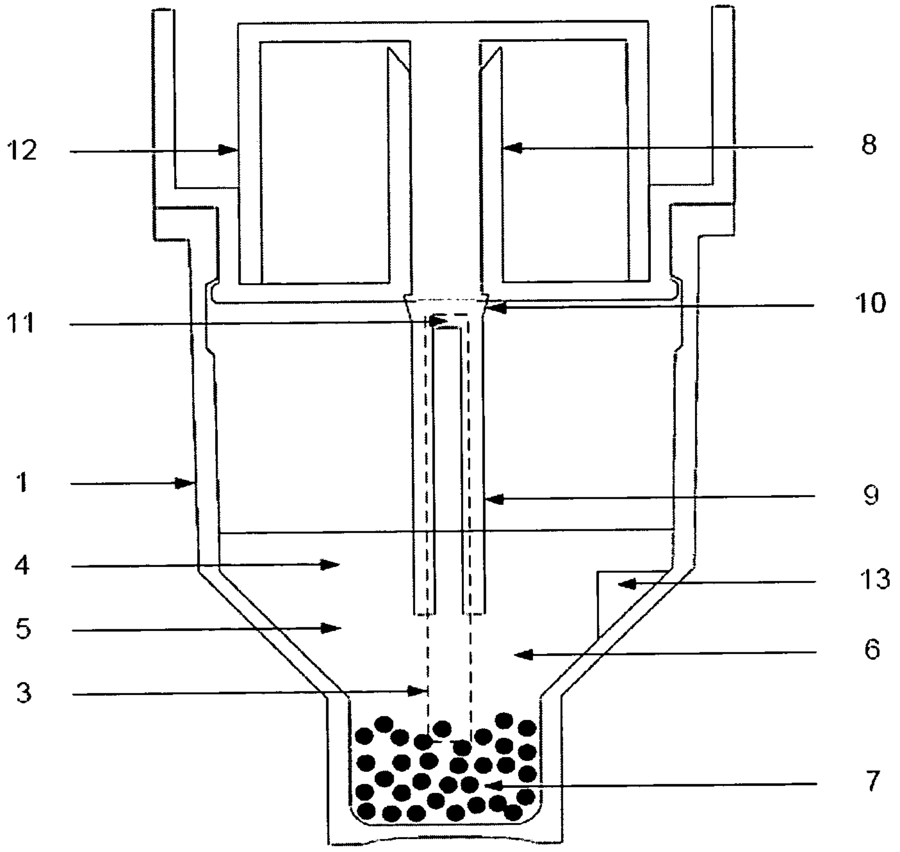
FIG. 2 illustrates the device according to the present invention in a pushed-together state, in which the pierceable membrane (2) has been pierced by the capillary tube (3) and the pierced hole has been sealed by the arm (9). The capillary tube (3) is placed in the sealed vessel (1).

FIG. 2 illustrates the device according to the invention in a pushed-together state, the pierceable membrane (2) being pierced by the capillary tube (3) and the pierced hole being sealed by the collar (10) on the arm (9). The capillary tube (3) is placed in the sealed vessel (1).

The device according to the invention may advantageously be used together with a magnetic detector by the device being placed in or in the immediate vicinity of an electric coil for detection of magnetic permeability $\mu$, or alternatively relative magnetic permeability $\mu_r$, or alternatively relative magnetic susceptibility ($\mu_r-1$).

The device according to the invention may advantageously be used together with an optical detector by the device being placed in the vicinity of a light source (for instance bulb, light emitting diode or laser) for measuring optical phenomena such as the changes of light absorption, light scattering, fluorescence and polarisation.

The device according to the invention may advantageously be used for detection of on the one hand chemical substances with high magnetic permeability and, on the other, chemical substances having approximately the same relative magnetic permeability as water, that is $\mu_r=1$, such as glucose, C-reactive protein (CRP and hsCRP), albumin, cystatin C, hemoglobin (Hb and HbA1C), myoglobin, troponin (I and T), CK-MB, creatine kinase (CK), d-dimer, BNP, proBNP, NT-proBNP, prothrombin, APTT, HCG, LH, FSH, PSA, TSH, T3, T4, AFP, CEA, lipoproteins (LDL and HDL), triglycerides, cholesterol, antibodies, *Streptococcus* A, *Heliobacter Pylori, Salmonella, Chlamydia, Giardia*, cholera, hepatitis (A, B and C) adenoviruses, rotaviruses, proteins, hormones, complementary factors, blood coagulation factors, cell-ligand interactions, cell-cell interactions, platelet aggregations, bacteria, cells, viruses, fungi, yeast, spores, phages, cells, cell organelles, DNA, RNA, which all require interaction with one or more magnetically influenceable reagents.

The device according to the invention may advantageously be used for a qualitative and respectively quantitative near patient one-time analysis (so-called Point-of-Care analysis) of glucose, C-reactive protein (CRP and hsCRP), albumin, cystatin C, hemoglobin (Hb and HbA1C), myoglobin, troponin (I and T), CK-MB, creatine kinase (CK), d-dimer, BNP, proBNP, NT-proBNP, prothrombin, APTT, HCG, LH, FSH, PSA, TSH, T3, T4, AFP, CEA, lipoproteins (LDL and HDL), triglycerides, cholesterol, antibodies, *Streptococcus* A, *Heliobacter Pylori, Salmonella, Chlamydia, Giardia*, cholera, hepatitis (A, B and C) adenoviruses, rotaviruses, proteins, hormones, complementary factors, blood coagulation factors, cell-ligand interactions, cell-cell interactions, platelet aggregations, bacteria, cells, viruses, fungi, yeast, spores, phages, cells, cell organelles, DNA, RNA, in various types of body fluids such as blood, plasma, urine, sweat, tears, lymph, cerebrospinal fluid and faeces.

The device according to the invention may advantageously be used for qualitative and respectively quantitative analysis of glucose, C-reactive protein (CRP and hsCRP), albumin, cystatin C, hemoglobin (Hb and HbA1C), myoglobin, troponin (I and T), CK-MB, creatine kinase (CK), d-dimer, BNP, proBNP, NT-proBNP, prothrombin, APTT, HCG, LH, FSH, PSA, TSH, T3, T4, AFP, CEA, lipoproteins (LDL and HDL), triglycerides, cholesterol, antibodies, *Streptococcus* A, *Heliobacter Pylori, Salmonella, Chlamydia, Giardia*, cholera, hepatitis (A, B and C) adenoviruses, rotaviruses, proteins, hormones, complementary factors, blood coagulation factors, cell-ligand interactions, cell-cell interactions, platelet aggregations, bacteria, cells, viruses, fungi, yeast, spores, phages, cells, cell organelles, DNA, RNA, in various types of industrial process control, quality control, research and laboratory work.

The device according to the invention may advantageously be marked with information such as analytical identification data and production lot number, last day of consumption, and date of production.

It is obvious to a person skilled in the art that the dimension information and volume information given in this description may easily be adjusted up and down without the spirit of the invention being changed. Moreover, used chemical substances may be replaced by other substances and in that case other analyses can be performed. All such modifications are considered to be within the scope of the invention.

The invention claimed is:

1. A detection method, comprising:

placing a device containing a measured sample volume of a sample in or in an immediate vicinity of an electric coil for detection of magnetic permeability $\mu$, relative magnetic permeability $\mu_r$, or relative magnetic susceptibility ($\mu_r-1$); and performing at least one selected from biochemical processing and analysis of the measured sample volume of a sample, wherein the device includes, a sealed vessel, the sealed vessel containing a liquid and at least one biochemically reactive substance, at least one thin pierceable membrane through which a capillary tube containing said measured sample volume of a sample can pass into said sealed vessel, and a capillary holder with an arm, in which said capillary tube is to be mounted and by means of which said capillary tube is to be inserted through said at least one thin pierceable membrane into said sealed vessel, wherein said arm has one selected from a conically shaped thickening on an outer diameter and a collar by which an opening of said at least one thin pierceable membrane is sealed after the insertion of the capillary tube, and wherein said sealed vessel further contains one selected from at least one marker substance and carrier particles forming a bottom sediment.

2. The method as claimed in claim 1, wherein sealed said vessel includes at least one internal wing configured for facilitating mixing of the liquid and the sample in the device.

3. The method as claimed in claim 2, wherein said at least one internal wing has a length and width in the range of 0.2-5 mm and a thickness in the range of 0.2-5 mm.

4. The method as claimed in claim 1, wherein said thin pierceable membrane is surrounded by the collar on an outside of the device after the insertion of the capillary tube.

5. The method as claimed in claim 1, wherein said arm includes a mounted capillary tube, or said arm is a unit shaped in the form of the capillary tube.

6. The method as claimed in claim 1, wherein said arm has an air vent in the form of one selected from a hole and a gap which extends parallel to the capillary tube and through which pressure equalization occurs so as to allow filling of said capillary tube.

7. The method as claimed in claim 1, wherein said capillary holder includes a cap.

8. The method as claimed in claim 1, wherein said sealed vessel, said at least one thin pierceable membrane, said capillary holder and said capillary tube are made of at least one material selected from transparent/non-transparent polymers, Delrin, Perspex, POM, polyvinylchloride, polyvinyl fluoride, Teflon, polyamide, polyacetal, nylon, polyethylene, polycarbonate, polystyrene, polypropylene and combinations thereof, or a material selected from glass, rubber, wood, paper and metal.

9. The method as claimed in claim 1, wherein said sample consists of a body fluid selected from blood, plasma, urine, sweat, tears, lymph, amniotic fluid, cerebrospinal fluid and feces.

10. The method as claimed in claim 1, wherein said at least one biochemically reactive substance consists one selected from monoclonal antibody, polyclonal antibody, enzyme, inorganic oxidising agents, inorganic reducing agents, metal ion, metal ion complex, protein, hormone, complementary factor, bacterium, cell, virus, fungus, yeast, spore, phage, cell organelle, peptide, DNA, RNA, coagulation inhibiting substance, cell lysing agents, antibiotics, tenside, active detergent, EDTA, adenosine 5' diphosphate, ristocetin, arachidonic acid, thrombin, epinephrine, platelet activator factor and a thrombin receptor agonist peptide (TRAP).

11. The method as claimed in claim 1, wherein said liquid consists of an aqueous solution containing at least one acidity regulating agent and at least one ionic strength adjusting agent.

12. The method as claimed in claim 1, wherein said at least one marker substance consists of a magnetically influenceable reagent selected from superparamagnetic nanoparticles, antibody-derivatized superparamagnetic nanoparticles, protein-derivatized superparamagnetic nanoparticles, polymer-derivatized superparamagnetic nanoparticles, peptide-derivatized superparamagnetic nanoparticles, DNA- or RNA-derivatized superparamagnetic nanoparticles, and carbohydrate-derivatized superparamagnetic nanoparticles, or the at least one marker substance consists of an optical, electric or radioactive reagent based on one selected from antibodies, enzymes, inorganic oxidising agents, inorganic reducing agents, metal ions and metal ion complexes, proteins, peptides, polymers, carbohydrates, complementary factors, blood coagulation factors, hormones, bacteria, cells, viruses, fungi, yeast, spores, phages, cell organelles, DNA, RNA, coagulation inhibiting substances, antibiotics, tensides and active detergents.

13. The method as claimed in claim 1, wherein, said carrier particles include antibodies, lectins, proteins, peptides, DNA or RNA, or nothing, bound to surfaces thereof, said carrier particles have a diameter between 0.5 micrometer and 5 mm and said carrier particles consist of one selected from hydrophilic silica, hydrophobic silica, glass, silicon dioxide, carbohydrates, ion exchangers, polymers, ceramic materials, proteins, and bacteria.

14. The method as claimed in claim 13, wherein the measured sample volume of said sample, when consisting of feces, is manually pressed into a cavity of the capillary tube without the use of capillary forces.

15. A method of analysis, comprising:

performing the detection method according to claim 1; and using the biochemical processing of said sample in said sealed vessel of the device for a qualitative and respectively quantitative near patient one-time analysis of one selected from glucose, C-reactive protein (CRP and hsCRP), albumin, cystatin C, hemoglobin (Hb and HbA1C), myoglobin, troponin (I and T), CK-MB, creatine kinase (CK), d-dimer, BNP, proBNP, NT-proBNP, prothrombin, APTT, HCG, LH, FSH, PSA, TSH, T3, T4, AFP, CEA, lipoproteins (LDL and HDL), triglycerides, cholesterol, antibodies, Streptococcus A, *Heliobacter Pylori, Salmonella, Chlamydia, Giardia*, cholera, hepatitis (A, B and C) adenoviruses, rotaviruses, proteins, hormones, complementary factors, blood coagulation factors, cell-ligand interactions, cell-cell interactions, platelet aggregations, bacteria, cells, viruses, fungi, yeast, spores, phages, cells, cell organelles, DNA, and RNA, in a body fluid selected from blood, plasma, urine, sweat, tears, lymph, cerebrospinal fluid and feces.

16. A method of analysis, comprising:

performing the detection method according to claim 1; and using the biochemical processing of said sample in said sealed vessel of the device for qualitative and respectively quantitative analysis of one selected from glucose, C-reactive protein (CRP and hsCRP), albumin, cystatin C, hemoglobin (Hb and HbA1C), myoglobin, troponin (I and T), CK-MB, creatine kinase (CK), d-dimer, BNP, proBNP, NT-proBNP, prothrombin, APTT, HCG, LH, FSH, PSA, TSH, T3, T4, AFP, CEA, lipoproteins (LDL and HDL), triglycerides, cholesterol, antibodies, Streptococcus A, *Heliobacter Pylori, Salmonella, Chlamydia, Giardia*, cholera, hepatitis (A, B and C) adenoviruses, rotaviruses, proteins, hormones, complementary factors, blood coagulation factors, cell-ligand interactions, cell-cell interactions, platelet aggregations, bacteria, cells, viruses, fungi, yeast, spores, phages, cells, cell organelles, DNA, and RNA.

17. The method as claimed in claim 1, wherein said liquid is an 0.1 M sodium phosphate aqueous solution having a pH of 7.

18. The method as claimed in claim 1, wherein said liquid is an 0.1 M sodium chloride aqueous solution.

* * * * *